(12) United States Patent
Csutak

(10) Patent No.: US 8,692,183 B2
(45) Date of Patent: Apr. 8, 2014

(54) METHOD AND APPARATUS FOR ESTIMATING A DOWNHOLE FLUID PROPERTY USING A MINIATURE INTEGRATED CIRCUIT SPECTROMETER

(75) Inventor: Sebastian Csutak, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 13/412,304

(22) Filed: Mar. 5, 2012

(65) Prior Publication Data

US 2013/0062514 A1 Mar. 14, 2013

Related U.S. Application Data

(60) Provisional application No. 61/449,973, filed on Mar. 7, 2011, provisional application No. 61/466,379, filed on Mar. 22, 2011.

(51) Int. Cl.
*G01V 5/00* (2006.01)
*G01V 5/08* (2006.01)

(52) U.S. Cl.
USPC ........................................ 250/262; 250/269.1

(58) Field of Classification Search
USPC .............................................. 250/262, 269.1
See application file for complete search history.

(56) References Cited

U.S. PATENT DOCUMENTS

| | | |
|---|---|---|
| 4,048,859 A | 9/1977 | Babcock |
| 4,171,908 A | 10/1979 | Robert et al. |
| 4,215,578 A | 8/1980 | Lautzenhiser |
| 4,233,847 A | 11/1980 | Walker |
| 5,177,555 A | 1/1993 | Stratton et al. |
| 5,202,745 A | 4/1993 | Sorin et al. |
| 5,410,917 A | 5/1995 | Giversen et al. |
| 5,912,457 A | 6/1999 | McQuaid |
| 6,437,916 B1 | 8/2002 | McLeod et al. |
| 6,567,174 B1 | 5/2003 | Barker et al. |
| 6,597,821 B1 | 7/2003 | Bohnert et al. |
| 6,779,402 B2 | 8/2004 | Rud et al. |
| 6,789,424 B2 | 9/2004 | Knudsen et al. |
| 6,816,534 B2 | 11/2004 | Flint et al. |

(Continued)

OTHER PUBLICATIONS

Limeres J, Calvo ML, Lakshminarayanan V, et al. Stress sensor based on light scattering by an array of birefringent optical waveguides 19th Congress of the International-Commission-for-Optics, Aug. 25-30, 2002.

(Continued)

*Primary Examiner* — David Porta
*Assistant Examiner* — Faye Boosalis
(74) *Attorney, Agent, or Firm* — Cantor Colburn LLP

(57) ABSTRACT

An apparatus for estimating a property of a downhole fluid includes a carrier that is conveyable in a borehole, a test cell carried by the carrier for capturing the downhole fluid, an integrated circuit positioned inside of the test cell, and an electromagnetic energy source that emits an electromagnetic energy beam having a first bandwidth. A first filter is formed on the integrated circuit in electromagnetic energy communication with the first electromagnetic energy beam. A flow path is formed in the integrated circuit wherein the flow path contains the downhole fluid in the test cell and is in electromagnetic energy communication with a portion of the electromagnetic energy beam. An electromagnetic energy detector is in electromagnetic energy communication with a portion of the electromagnetic energy beam that has interacted with the downhole fluid for estimating the property of the downhole fluid.

20 Claims, 5 Drawing Sheets

(56) References Cited

U.S. PATENT DOCUMENTS

| | | | |
|---|---|---|---|
| 6,913,079 B2 * | 7/2005 | Tubel | 166/250.01 |
| 7,595,876 B2 | 9/2009 | DiFoggio | |
| 7,751,044 B2 | 7/2010 | Csutak | |
| 7,781,737 B2 | 8/2010 | Zhdaneev | |
| 2004/0033017 A1 * | 2/2004 | Kringlebotn et al. | 385/31 |
| 2004/0129867 A1 | 7/2004 | Mackey | |
| 2007/0120051 A1 | 5/2007 | DiFoggio et al. | |
| 2007/0126594 A1 | 6/2007 | Atkinson et al. | |
| 2010/0079753 A1 | 4/2010 | Hehlen | |

OTHER PUBLICATIONS

Up-Conversion Luminescence in Thulium Doped Barium Titanate Inverted Opal, Cao Jing, Zhoud Ji, Li Bo, Fu Ming and Zong Ruilong, Key Engineering Materials, vols. 336-338 (2007) pp. 561-563.
International Search Report and Written Opinion for PCT Application No. PCT/US2012/028033, dated Oct. 10, 2012, pp. 1-11.

* cited by examiner

METHOD AND APPARATUS FOR ESTIMATING A DOWNHOLE FLUID PROPERTY USING A MINIATURE INTEGRATED CIRCUIT SPECTROMETER

CROSS REFERENCE TO RELATED APPLICATIONS

This application claims the benefit of an earlier filing date from U.S. Provisional Application Ser. No. 61/449,973 filed Mar. 7, 2011 and U.S. Provisional Application Ser. No. 61/466,379 filed Mar. 22, 2011, the entire disclosures of which are incorporated herein by reference.

BACKGROUND

1. Technical Field

The present disclosure generally relates to well bore tools and in particular to an apparatus and methods for downhole spectroscopy.

2. Background Information

Oil and gas wells have been drilled at depths ranging from a few thousand feet to as deep as 5 miles. Wireline and drilling tools often incorporate various sensors, instruments and control devices in order to carry out downhole operations. These operations may include formation testing, fluid analysis, and tool monitoring and control. In the oil and gas industry, formation testing tools have been used for monitoring formation pressures along a wellbore in a hydrocarbon bearing formation or reservoir, obtaining formation fluid samples from the wellbore and predicting performance of the reservoirs around the wellbore. Such formation testing tools typically contain an elongated body having an elastomeric packer that is sealingly urged against the zone of interest in the wellbore to collect formation fluid samples in storage test cells placed in the tool.

During drilling of a wellbore, a drilling fluid ("mud") is used to facilitate the drilling process and to maintain a pressure in the wellbore greater than the fluid pressure in the formations surrounding the wellbore. This is particularly important when drilling into formations where the pressure is abnormally high. If the fluid pressure in the borehole drops below the formation pressure, there is a risk of blowout of the well. As a result of this pressure difference, the drilling fluid penetrates into or invades the formations for varying radial depths (referred to generally as invaded zones) depending upon the types of formation and drilling fluid used. The formation testing tools retrieve formation fluids from the desired formations or zones of interest, test the retrieved fluids to ensure that the retrieved fluid is substantially free of mud filtrates, and collect such fluids in one or more test cells associated with the tool. The collected fluids are brought to the surface and analyzed to determine properties of such fluids and to determine the condition of the zones or formations from where such fluids have been collected.

SUMMARY

The following presents a general summary of several aspects of the disclosure in order to provide a basic understanding of at least some aspects of the disclosure. This summary is not an extensive overview of the disclosure. It is not intended to identify key or critical elements of the disclosure or to delineate the scope of the claims. The following summary merely presents some concepts of the disclosure in a general form as a prelude to the more detailed description that follows.

An apparatus is disclosed including but not limited to an integrated circuit positioned inside of the a cell; an electromagnetic energy source that emits an electromagnetic energy beam having a first bandwidth; a first filter formed on the integrated circuit in electromagnetic energy communication with the first electromagnetic energy beam, that filters the electromagnetic energy beam and passes through a portion of the electromagnetic energy beam having a second bandwidth that is narrower than the first bandwidth; a flow path formed in the integrated circuit wherein the flow path contains the downhole fluid in the test cell and is in electromagnetic energy communication with a portion of the electromagnetic energy beam; and an electromagnetic energy detector in electromagnetic energy communication with a portion of the electromagnetic energy beam that has interacted with the downhole fluid for estimating the property of the downhole fluid. A method using the apparatus is disclosed.

BRIEF DESCRIPTION OF THE DRAWINGS

For a detailed understanding of the present disclosure, reference should be made to the following detailed description of the several non-limiting embodiments, taken in conjunction with the accompanying drawings, in which like elements have been given like numerals and wherein.

DETAILED DESCRIPTION

Figure 1:
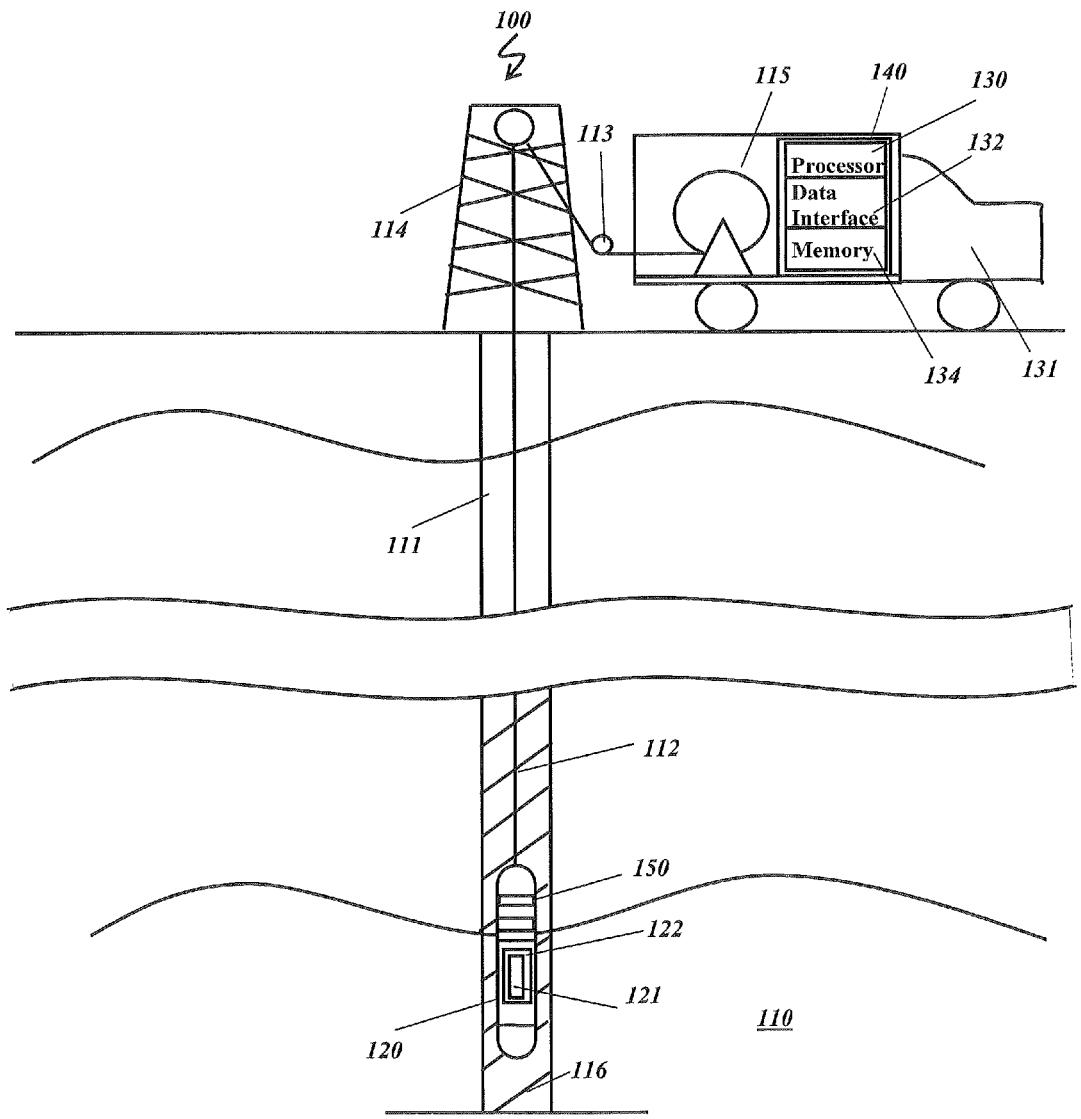
FIG. 1 is a schematic diagram of a particular illustrative embodiment deployed on a wire line in a downhole environment.

The present disclosure uses terms, the meaning of which terms will aid in providing an understanding of the discussion herein. As used herein, high temperature refers to a range of temperatures typically experienced in oil production well boreholes. For the purposes of the present disclosure, high temperature and downhole temperature include a range of temperatures from about 100 degrees C. to about 290 degrees C. and above.

The term "carrier" as used herein means any device, device component, combination of devices, media and/or member that may be used to convey, house, support or otherwise facilitate the use of another device, device component, combination of devices, media and/or member. Exemplary non-limiting carriers include wire lines and drill strings of the coiled tube type, of the jointed pipe type and any combination or portion thereof.

A "downhole fluid" as used herein includes any gas, liquid, flowable solid and other materials having a fluid property. A downhole fluid may be natural or man-made and may be transported downhole or may be recovered from a downhole location. Non-limiting examples of downhole fluids include but are not limited to drilling fluids, return fluids, formation fluids, production fluids containing one or more hydrocarbons, oils and solvents used in conjunction with downhole tools, water, brine and combinations thereof.

"Processor" as used herein means any device that transmits, receives, manipulates, converts, calculates, modulates, transposes, carries, stores or otherwise utilizes data. In several non-limiting aspects of the disclosure, a processor includes but is not limited to a computer that executes programmed instructions stored on a tangible non-transitory computer readable medium for performing various methods.

Q as used herein is a dimensionless parameter that describes how under-damped an oscillator or resonator is, or equivalently, characterizes a resonator's bandwidth relative to its center frequency. Higher Q indicates a lower rate of energy loss relative to the stored energy of the oscillator; the oscillations die out more slowly. A pendulum suspended from a high-quality bearing, oscillating in air, has a high Q, while a pendulum immersed in oil has a low one. Oscillators with high quality factors have low damping so that they ring longer. The optical Q is equal to the ratio of the resonant frequency to the bandwidth of the cavity resonance. The average lifetime of a resonant photon in the cavity is proportional to the cavity's Q.

Portions of the present disclosure, detailed description and claims may be presented in terms of logic, software or software implemented illustrative embodiments that are encoded on a variety of tangible non-transitory computer readable storage media including, but not limited to tangible non-transitory computer readable media, program storage media or computer program products. Such media may be handled, read, sensed and/or interpreted by an information processing device. Those skilled in the art will appreciate that such media may take various forms such as cards, tapes, magnetic disks (e.g., floppy disk or hard disk drive) and optical disks (e.g., compact disk read only memory ("CD-ROM") or digital versatile (or video) disk ("DVD")). Any embodiment disclosed herein is for illustration only and not by way of limiting the scope of the disclosure or claims.

In a particular illustrative embodiment, a miniature integrated circuit spectrometer is disclosed for estimating a property of a downhole fluid. In a particular embodiment, the miniature spectrometer is used to estimate a property of a downhole fluid by detecting the presence of chemical components in the downhole fluid. In a particular illustrative embodiment, an optical pump laser is provided in the 600-1200 nanometer range to introduce electromagnetic energy into a rare earth doped laser gain cavity formed on an integrated circuit. The laser gain medium generates an electromagnetic beam that is directed toward a flow path formed on the integrated circuit. In a particular embodiment, the electromagnetic energy from the laser gain cavity is introduced to the downhole fluid in a flow path on the integrated circuit. A photonic crystal filter is also provided on the integrated circuit. The photonic crystal receives and filters electromagnetic energy that has interacted with a downhole fluid in the flow path. Electromagnetic energy received from the downhole fluid that passes through the photonic crystal filter is sensed by an electromagnetic energy sensor. The electromagnetic energy sensed by the electromagnetic sensor is analyzed to determine the property of the downhole fluid. Non-limiting examples of the rare earth doped laser gain cavity are a rare earth doped inverted opal laser and a rare earth doped photonic crystal laser. In a particular embodiment an inverted rare earth laser can be used such as described in *Up-Conversion Luminescence in Thulium Doped Barium Titanate Inverted Opal*, Cao Jing, Zhoud Ji, Li Bo, Fu Ming and Zong Ruilong, *Key Engineering Materials*, Vols. 336-338 (2007) PP. 561-563. Any laser may be used that is suitable in accordance with the disclosure. The lasing wavelength of the photonic crystal rare earth doped laser gain cavity can be adjusted to emit electromagnetic energy suitable to detect several chemicals of interest in situ downhole in a downhole fluid. Such chemicals of interest may include but are not limited to C1 methane, C2 ethane, C3 propane, C4 butane and C5 pentane of H2S (hydrogen sulfide), H2S and CO2.

In a particular embodiment, an electro optic modulator (EOM) is provided to tune a frequency of electromagnetic energy emitted by a photonic crystal rare earth doped laser gain cavity and a photonic crystal filter. In another embodiment the EOM is integrated into the miniature integrated circuit spectrometer. An EOM is an optical device in which a signal-controlled element displaying electro-optic effect is used to modulate a beam of electromagnetic energy. The modulation may be imposed on the phase, frequency, amplitude, or polarization of the modulated beam. The EOM is used to apply a change in stress, current supply or temperature to the photonic crystal rare earth doped laser to change the frequency of electromagnetic energy emitted by the laser gain cavity or photonic crystal filter to scan for several wavelengths of interest in determining the property of the fluid. In another particular embodiment a plurality of lasers, which can be photonic crystals, each having a separate wavelength, are used to provide several different wavelengths.

Photonic crystal filters and lasers include but are not limited to periodic dielectric or metallo-dielectric nanostructures that affect the propagation of electromagnetic waves (EM) in the same way as the periodic potential in a semiconductor crystal affects the electron motion by defining allowed and forbidden electronic energy bands. Essentially, photonic crystals contain regularly repeating internal regions of high and low dielectric constant. Photons (behaving as waves) propagate through this structure—or not—depending on their wavelength. Wavelengths of electromagnetic energy that are allowed to travel are known as modes, and groups of allowed modes form bands.

Disallowed bands of wavelengths are called photonic band gaps. This gives rise to distinct optical phenomena such as inhibition of spontaneous emission, high-reflecting omni-directional mirrors and low-loss-wave guiding, amongst others. It is essentially a natural photonic crystal, although it does not have a complete photonic band gap. The opal is a natural periodic microstructure responsible for its iridescent color. The most frequently used laser-active rare earth ions and host media together with typical emission wavelength ranges are shown in the Table 1.

TABLE 1

Common Laser-Active Rare Earth Ions And Host Media And Example Emission Wavelengths

| Ion Name | Common Host Media | Example Emission Wavelengths |
|---|---|---|
| neodymium ($Nd^{3+}$) | YAG, $YVO_4$, YLF, silica | 1.03-1.1 µm, 0.9-0.95 µm, 1.32-1.35 µm |
| ytterbium ($Yb^{3+}$) | YAG, tungstates, silica | 1.0-1.1 µm |
| erbium ($Er^{3+}$) | YAG, silica | 1.5-1.6 µm, 2.7 µm, 0.55 µm |
| thulium ($Tm^{3+}$) | YAG, silica, fluoride glasses | 1.7-2.1 µm, 1.45-1.53 µm, 0.48 µm, 0.8 µm |
| holmium ($Ho^{3+}$) | YAG, YLF, silica | 2.1 µm, 2.8-2.9 µm |
| praseodymium ($Pr^{3+}$) | silica, fluoride glasses | 1.3 µm, 0.635 µm, 0.6 µm, 0.52 µm, 0.49 µm |
| cerium ($Ce^{3+}$) | YLF, LiCAF, LiLuF, LiSAF, and similar fluorides | 0.28-0.33 µm |

Ytterbium- and neodymium-doped gain media for lasers and erbium-doped fibers for erbium-doped fiber amplifiers. Other rare-earth-doped ions are yttrium ($Y^{3+}$), samarium ($Sm^{3+}$), europium ($Eu^{3+}$), gadolinium ($Gd^{3+}$), terbium ($Tb^{3+}$), dysprosium ($Dy^{3+}$), and lutetium ($Lu^{3+}$) which are also used sometimes as a codopant, e.g. for quenching the population in certain energy levels by energy transfer processes, or for realizing saturable absorbers, or as optically passive constituents of laser crystals.

There is a wide range of crystalline media (laser crystals) which can serve as host media for laser-active rare earth ions. Frequently used crystal materials are certain oxides (e.g. YAG), vanadates ($YVO_4$, $GdVO_4$), tungstates (KGW, KYW), fluorides (YLF, CaF), borates (BOYS), and apatites (S-FAP, SYS). Numerous scholarly articles on gain media and laser crystals discuss a number of important properties of host crystals. Compared with crystals, rare-earth-doped glasses usually allow for a larger gain bandwidth and thus larger wavelength tuning ranges, and also shorter ultra-short pulses with passive mode locking. Such glasses are used in the form of bulk pieces or optical fibers (e.g. rare-earth-doped silica fibers). The high optical confinement in fibers allows operation even on "difficult" laser transitions with low gain efficiency. Special fibers, e.g., fibers made on fluoride glass have particularly low phonon energies, leading to good mid-infrared transmission and long metastable level lifetimes. They are also often used for up conversion lasers. Numerous scholarly articles are also available on rare-earth-doped fibers, laser crystals versus glasses, and ceramic gain media.

Rare-earth-doped gain media have in common that the pump and laser transitions are so-called "weakly allowed transitions" with fairly small oscillator strength. A consequence of this is that the upper-state lifetimes of a range of microseconds to milliseconds, so that substantial amounts of energy can be stored in such media. Depending on the phonon energies of the host medium, some of the level lifetimes can be strongly quenched by multi-phonon transitions. Such effects are minimized in low-phonon-energy host media such as fluoride fibers. Quenching effects can be welcome if they depopulate the lower laser level, thus preventing or reducing reabsorption, or if they help to populate the upper laser level within the pumping process. Various kinds of interactions, in particular dipole-dipole interactions, allow energy transfer between different rare earth ions either of the same species or of different species. This is exploited e.g. in erbium-ytterbium-co doped fibers, where the pump radiation is dominantly absorbed by ytterbium ions and mostly transferred to erbium ions.

Turning now to FIG. 1, FIG. 1 is a schematic representation of a wireline formation testing system 100 for estimating a property of a downhole fluid. FIG. 1 shows a wellbore 111 drilled in a formation 110. The wellbore 111 is shown filled with a drilling fluid 116, which is also is referred to as "mud" or "wellbore fluid." The term "connate fluid" or "natural fluid" herein refers to the fluid that is naturally present in the formation, exclusive of any contamination by the fluids not naturally present in the formation, such as the drilling fluid. Conveyed into the wellbore 111 at the bottom end of a wireline 112 is a formation evaluation tool 120 that includes but is not limited to an analysis module 150 and a miniature integrated circuit spectrometer 121 made according to one or more embodiments of the present disclosure for in-situ estimation of a property of the fluid withdrawn from the formation. The formation evaluation tool 120 acts a carrier for the miniature integrated circuit spectrometer 121 and a sample tank 122 also referred to herein as a test cell. Exemplary embodiments of various miniature integrated circuit spectrometers are described in more detail in reference to FIGS. 3-5. The wireline 112 typically is an armored cable that carries data and power conductors for providing power to the tool 120 and a two-way data communication link between a tool processor in the analysis module 150 and a surface controller 140 placed in surface unit, which may be a mobile unit 131, such as a logging truck. The surface controller 140 and analysis module 150 each may include but are not limited to a processor 130, data interface 132 and non-transitory computer readable media 134.

The wireline 112 typically is carried from a spool 115 over a pulley 113 supported by a derrick 114. The controller 140 and analysis module 150 are each in one aspect, a computer-based system, which may include one or more processors such as a microprocessor, that may include but is not limited to one or more non-transitory data storage devices, such as solid state memory devices, hard-drives, magnetic tapes, etc.; peripherals, such as data input devices and display devices; and other circuitry for controlling and processing data received from the tool 120. The surface controller 140 and analysis module 150 may also include but are not limited to one or more computer programs, algorithms, and computer models, which may be embedded in the non-transitory computer-readable medium that is accessible to the processor for executing instructions and information contained therein to perform one or more functions or methods associated with the operation of the formation evaluation tool 120. Thus processing may occur at the surface particular embodiment, or in situ in other embodiments. Processing may be split between the surface and in situ in other embodiments.

The test cell may include but is not limited to a downhole fluid sample tank 122 and a flow line 211 (shown in FIG. 2) through which downhole fluid flows into the downhole fluid sample tank 122. The test cell may be any suitable downhole fluid receptacle in accordance with the disclosure. At least a portion of the miniature integrated circuit spectrometer 121 is immersed in the downhole fluid in the test cell and used for in situ or surface analysis of the downhole fluid, including but not limited to estimating a property of the downhole fluid. Additional downhole test devices for estimating a property of the downhole fluid may be included in the formation evaluation tool 120. Any test device may be included in accordance with disclosure, including but not limited to nuclear magnetic resonance (NMR) spectrometers, pressure, temperature, optomechanical resonators and electromechanical resonators for estimating density and viscosity of a downhole fluid.

Figure 2:
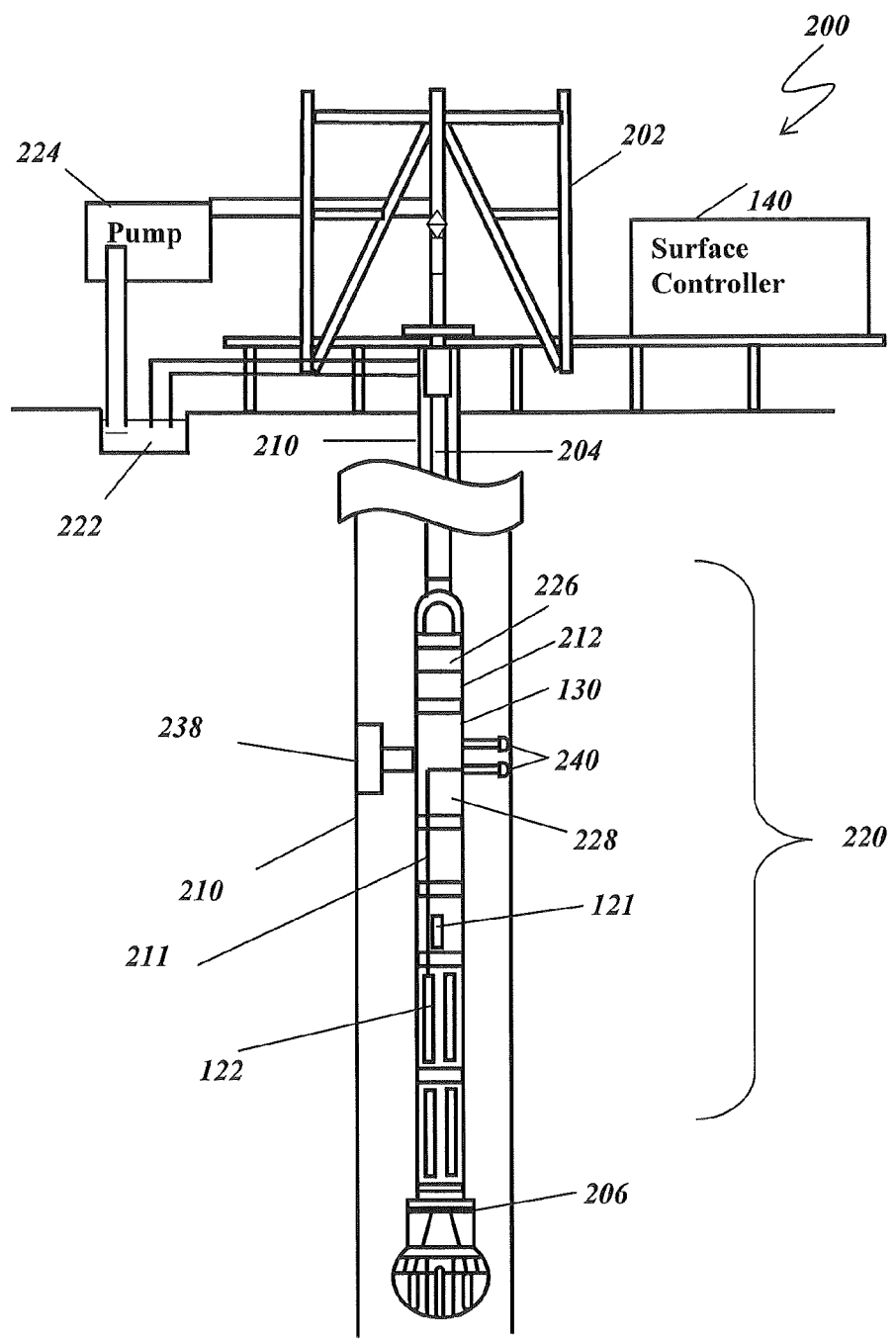
FIG. 2 is a schematic diagram of another particular illustrative embodiment deployed on a drill string in a monitoring while drilling environment.

FIG. 2 depicts a non-limiting example of a drilling system 200 in a measurement-while-drilling (MWD) arrangement according to one embodiment of the disclosure. A derrick 202 supports a drill string 204, which may be a coiled tube or drill pipe. The drill string 204 may carry a bottom hole assembly (BHA) 220 and a drill bit 206 at a distal end of the drill string 204 for drilling a borehole 210 through earth formations. Drilling operations according to several embodiments may include pumping drilling fluid or "mud" from a mud pit 222, and using a circulation system 224, circulating the mud through an inner bore of the drill string 204. The mud exits the drill string 204 at the drill bit 206 and returns to the surface through an annular space between the drill string 204 and inner wall of the borehole 210.

In the non-limiting embodiment of FIG. 2, the BHA 220 may include a formation evaluation tool 120, a power unit 226, a tool processor 212 and a surface controller 140. Any suitable power unit may be used in accordance with the disclosure. Non-limiting examples of suitable power units include but are not limited to a hydraulic, electrical, or electro-mechanical and combinations thereof. The tool 120 may carry a fluid extractor 228 including a probe 238 and opposing feet 240. In several embodiments to be described in further detail below, the tool 120 includes but is not limited to a downhole miniature integrated circuit spectrometer system 121. A flow line 211 connects fluid extractor 228 to sample tank 122 and miniature integrated circuit spectrometer 121. Downhole fluid flows from the formation into the sample tank from fluid extractor through the flow line into the sample tank. The miniature integrated circuit spectrometer may be used in either the while-drilling embodiments or in the wireline embodiments for in situ or surface estimation of a property of the downhole fluid.

Those skilled in the art with the benefit of the present disclosure will recognize that the several embodiments disclosed are applicable to a downhole fluid production facility without the need for further illustration. The several examples described below and shown in FIG. 3-5 may be implemented using a wireline system as described above and shown in FIG. 1, may be implemented using a while-drilling system as described above and shown in FIG. 2 or may be implemented in a production facility to monitor production fluids.

Figure 3:
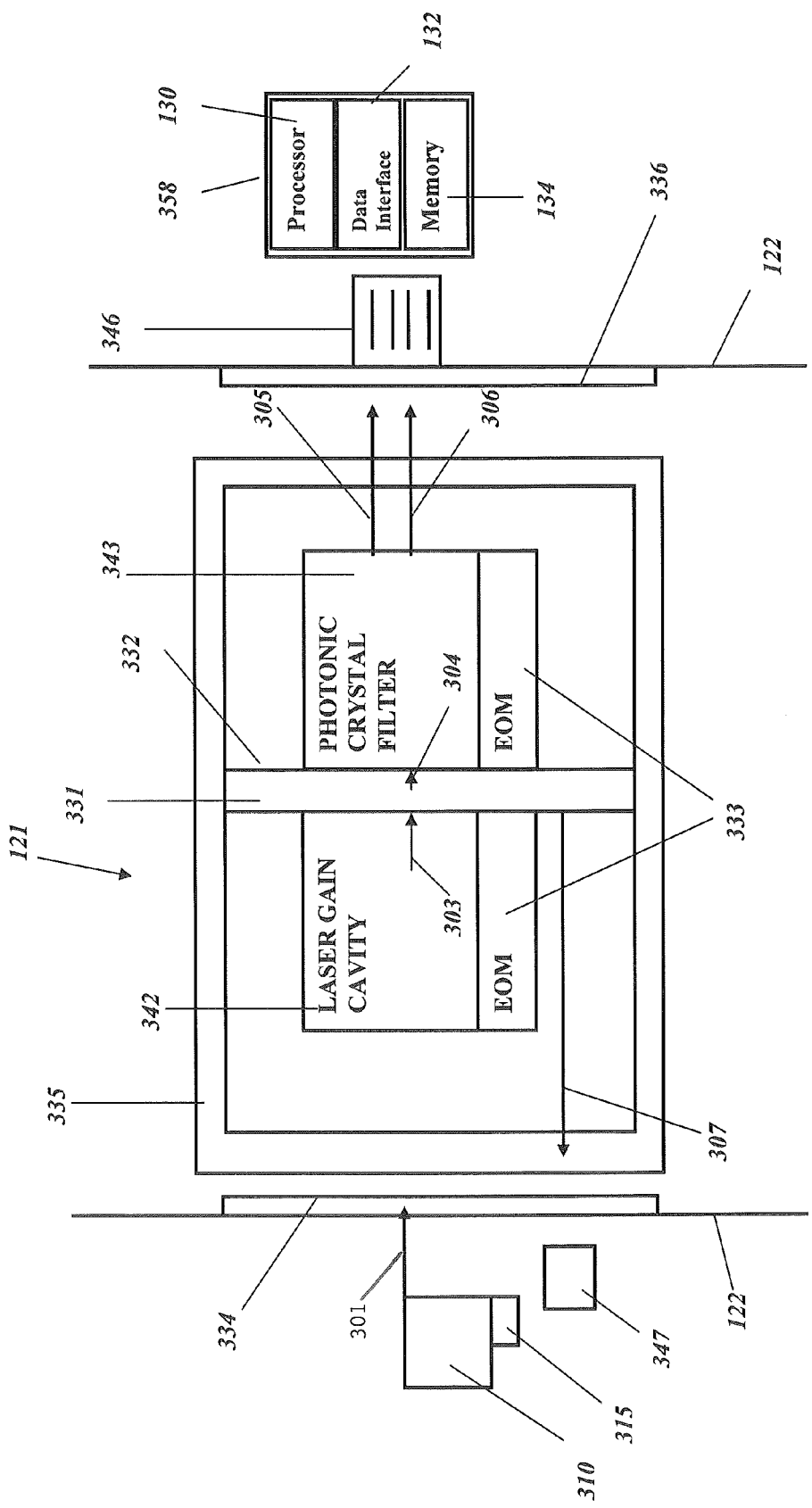
FIG. 3 is a schematic illustration of a particular illustrative embodiment according to the disclosure.

FIG. 3 shows a schematic diagram of a module of a particular illustrative embodiment of a miniature integrated circuit spectrometer 121 for use in a downhole tool, such as the tool 120. It is shown to include certain elements or components of the miniature integrated circuit spectrometer 121 made according to one exemplary embodiment. A portion 331 of the downhole fluid entering the tool 120 is passed into or through sample tank flow line 211 to the test cell shown as sample tank 122 as a downhole fluid. The downhole fluid flows into flow path 332 formed in the miniature integrated circuit spectrometer. The miniature integrated circuit spectrometer can also be deployed in downhole fluid in the test cell or in the fluid flow line 211. The term flow path refers to a flow channel formed on the miniature integrated circuit spectrometer for containing and analyzing downhole fluid. In a particular embodiment, the flow path is in the nanometer range wherein microfluidics properties apply. In another particular embodiment, the flow path is on the order about 1 millimeter wide wherein microfluidics principles do not apply.

The term "test cell" as used herein is used to synonymously refer to the sample tank flow line 211 and the sample tank 122 both of which contain downhole fluid. The test cell, in one aspect, may include a first window 334 for ingress and egress of electromagnetic energy into downhole fluid 331 in the test cell. Electromagnetic energy is emitted from an electromagnetic source 310. In a particular embodiment, a second window 336, generally on the opposite side of the first window, for allowing electromagnetic energy to pass out of the downhole fluid for measurement by an electromagnetic sensor and analysis by a processor. The test cell may hold the downhole fluid or may allow it to pass there through.

In a particular embodiment, the electromagnetic source is an electromagnetic energy pump 310, in one particular illustrative embodiment, is a laser pump that emits electromagnetic energy 301 introduced to the electromagnetic energy source 342, which can be a laser gain cavity that emits electromagnetic energy centered about a particular frequency. In another illustrative embodiment the electromagnetic source is a super luminescent light emitting diode (SLED). In another embodiment the SLED can be used without the laser gain cavity to generate electromagnetic energy for introduction into the downhole fluid in the flow path. In another illustrative embodiment the electromagnetic source is a fluorescent electromagnetic energy source which may be used without the laser gain cavity. In a particular embodiment, any electromagnetic energy source is used with the laser gain cavity, when the electromagnetic energy source provides a desired frequency and energy density for use as described herein. In a particular embodiment, the electromagnetic energy emitted by the electromagnetic energy source 310, enters the laser gain cavity 342 wherein a particular frequency of light is amplified and emitted from the laser gain cavity as electromagnetic energy beam 303. Electromagnetic energy beam 303 is directed to downhole fluid 331 in flow path 332. After the electromagnetic energy beam 303 interacts with downhole fluid 331, it is received as electromagnetic energy 304 by photonic crystal filter 343. The photonic crystal filter substantially attenuates electromagnetic energy outside of a bandwidth centered on a particular frequency. The energy within the bandwidth of the photonic crystal filter is passed through the photonic crystal filter as electromagnetic energy beam 305 and is received by electromagnetic energy detector 346. The Electromagnetic energy emitted by the electromagnetic energy source and filtered by the photonic crystal filter is labeled 305 after it passes through the downhole fluid 331, through photonic crystal filter 343 and out of the test cell window 336 after interacting with the downhole fluid 331. The interaction of the electromagnetic energy 303 with the downhole fluid the flow path may include but is not limited to transmittance electromagnetic energy 305, which travels through the downhole fluid in the flow path, fluorescent response electromagnetic energy 306 which is generated in the downhole fluid in response to a fluorescent stimulus frequency electromagnetic energy, Raman scattered electromagnetic energy 306 which is generated in the downhole fluid in response to a Raman stimulus frequency electromagnetic energy and reflected electromagnetic energy 307 of the electromagnetic energy 303. The electromagnetic energy source 342 in on one non-limiting embodiment can be a laser gain cavity. In a preferred embodiment, the laser gain cavity, flow path and photonic crystal filter are all formed on a miniature integrated circuit spectrometer having a volume of less than 1 cubic centimeter. In other alternative embodiments the electromagnetic energy pump and electromagnetic energy source can be any electromagnetic energy source in accordance with the disclosure.

Figure 4:
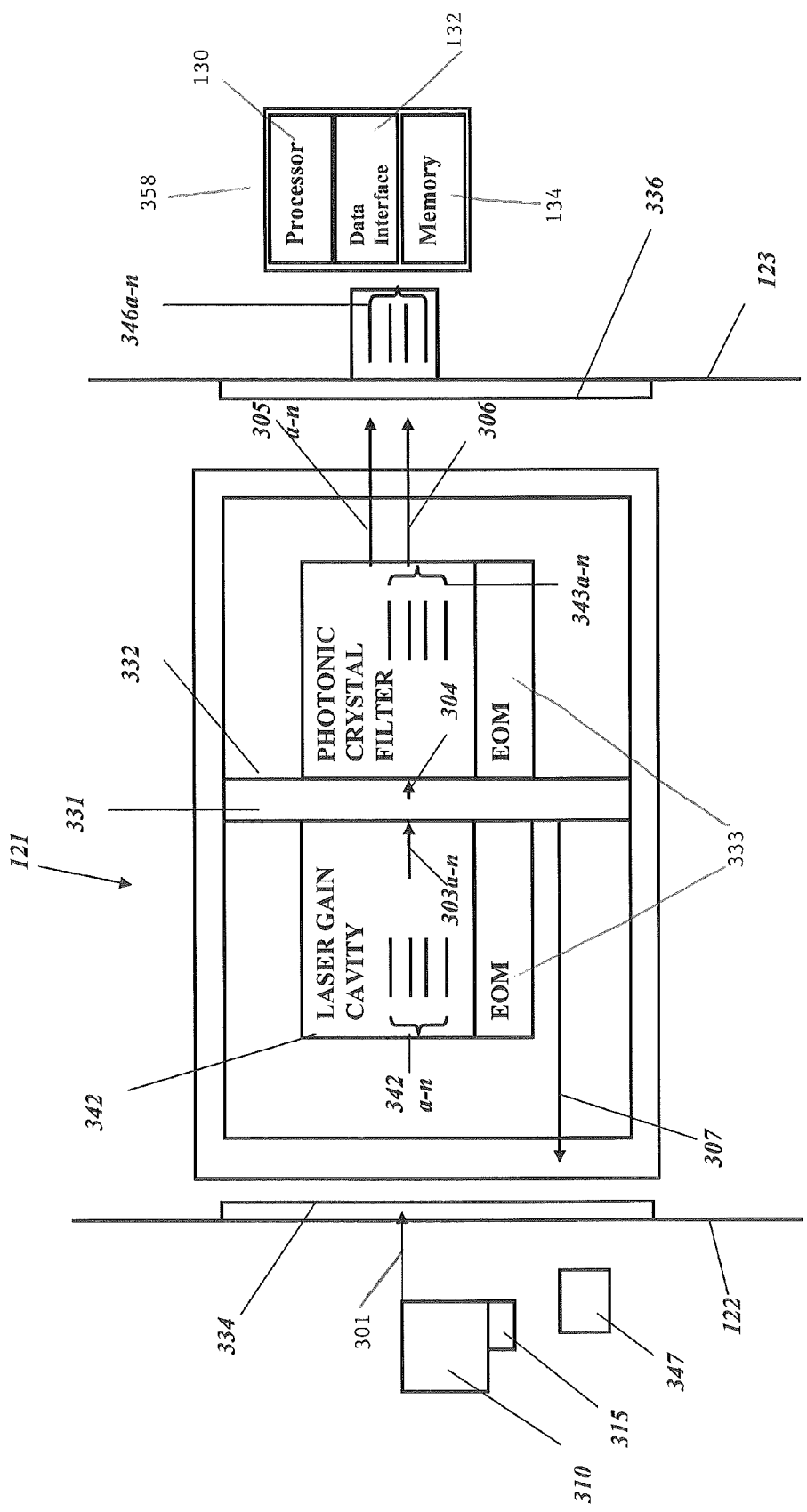
FIG. 4 is a schematic illustration of another particular illustrative embodiment according to the disclosure.

FIG. 4 is a schematic diagram of a portion of another particular illustrative embodiment of a miniature integrated circuit spectrometer 121 for estimating a property of the downhole fluid in a downhole tool, such as tool 120 shown in FIGS. 1 and 2. Turning now to FIG. 4, in another embodiment, the electromagnetic energy source 342 is one or more laser gain cavities that includes a number of laser gain cavities 342a-342n that can include but are not limited to a plurality of rare earth doped photonic laser gain cavities 342a-342n, wherein each rare earth doped laser gain cavity is tuned by doping the photonic laser gain cavity on the integrated circuit 330 with a particular rare earth element to provide electromagnetic energy output 303 corresponding to a distinct wavelength. Each laser gain cavity 342a-342n in the laser gain cavity array can be designated to correspond to a spectrometric analysis channel at a particular frequency in the spectrometer. In another particular embodiment, an electromagnetic energy spectrum of interest may range from ultraviolet wavelength to infrared wavelength. The electromagnetic source may be designed to emit fluorescent stimulus electromagnetic energy at a first frequency to cause the downhole fluid 331 in the flow path 332 to emit fluorescent electromagnetic energy at a second frequency.

In another particular embodiment, the electromagnetic spectrum may be divided into a desired number of relatively narrow wavelength bands, each wavelength band having a particular center wavelength. Each such band may correspond to output electromagnetic energy from a separate laser gain cavity. The electromagnetic energy source 342 may include a fluorescent source that generates fluorescent electromagnetic energy which is introduced into the downhole fluid in the flow path. The electromagnetic energy source 342 may include a Raman stimulus frequency source that generates electromagnetic energy at a Raman stimulus frequency into the downhole fluid in the flow path that causes the downhole fluid in the flow path to emit Stokes and anti-Stokes frequency electromagnetic energy.

In a particular illustrative embodiment, each laser gain cavity is a doped silicon wafer fabricated to contain a specific pattern of air spaces in a suitable semiconductor material such that each laser gain cavity 342a-342n is tuned to provide output electromagnetic energy that corresponds to a specific center wavelength. In another particular illustrative embodiment, the total number of laser gain cavities may correspond to the total number of channels that comprise the desired spectrum of the miniature integrated circuit spectrometer. For example, if the spectrum of interest ranges from 200 nm to 2500 nm and the total desired channels equal fifty, then fifty laser gain cavities are formed on the miniature integrated circuit spectrometer and tuned to cover the entire chosen spectrum of 200-2500 nm. In another particular illustrative embodiment, a number of laser gain channels are packed into a relatively small space by using photonic crystal optical fibers. Such fibers, in one aspect, may contain many elongated air holes parallel to the fiber axis that run the length of the fiber. Such fibers are sometimes referred to as "holey fibers."

In another particular illustrative embodiment, a group of lasers which may be rare earth doped laser gain cavities may be tuned to different wavelengths of interest. For example, a particular laser gain cavity may be tuned to emit electromagnetic energy transmitted through the downhole fluid in the flow path that corresponds to a particular wavelength band where the refractive index or absorption is of interest, such as for oil, water, gas, etc. In one aspect, each laser, which in a particular embodiment is a rare earth doped laser gain cavity may be configured to contain a unique pattern of air spaces in a substrate (such as solid-state substrate) to provide output electromagnetic energy corresponding to a particular wavelength. The array of lasers, which in a particular embodiment are rare earth doped laser gain cavities, may be housed in one or more common modules for use in the tool downhole. The modules, including but not limited to the miniature integrated circuit spectrometer when desired, are cooled by a cooling device 335, such as a Dewar flask or using another type of cooling device, including but not limited to an EOM, sorption cooler, cruogenic cooler or thermoelectric cooler. In another particular illustrative embodiment the laser gain cavities or other laser types are provided with a tuning device such as an EOM 333 to thermally adjust the frequency of each of the laser's electromagnetic energy output. Non-limiting examples of the thermal device 333 include but are not limited to a Dewar cooling flask and a resistive heater. Any thermal device made in accordance with the disclosure is suitable.

In another particular illustrative embodiment, an EOM 333 is provided as turning device to tune or change the frequency of electromagnetic energy out put by a laser source, such as the laser gain cavity 342. The laser source may be any suitable type electromagnetic source including but not limited to a SLED, a Fabry Perot tunable laser operating at a fixed or variable frequency, a tunable laser including but not limited to the lasers, laser gain cavities, photonic crystals and other laser types described herein. In a particular embodiment, the EOM applies thermal energy to the tunable laser source or laser pump to change the frequency of the electromagnetic energy emitted by the tunable laser source and laser pump. In a particular embodiment, the EOM applies variable current to the tunable laser source to change the frequency of the electromagnetic energy emitted by the tunable laser source. In another embodiment the EOM applies mechanical stress from a mechanical or piezoelectric device to change the frequency of the electromagnetic energy emitted by the laser source. The EOM is also used to control the frequency of electromagnetic energy emitted by the laser pump.

In a particular embodiment the EOM is integrated on a silicon wafer with the laser source for control of each of the laser source's output electromagnetic energy wavelength. In another illustrative embodiment, the EOM applies current, thermal energy or stress to more than one laser at a time to tune the laser sources in groups of 2 or more. In another illustrative embodiment, the EOM tunes each laser source in a group of laser sources one at a time individually.

In a particular embodiment, the electromagnetic energy from the laser gain cavity interacts with the downhole fluid in the flow path and subsequently filtered by a photonic crystal filter 343. The frequency of the electromagnetic energy emitted from laser gain cavity is determined by the size of the laser gain cavity, doping and the EOM associated with the laser gain cavity. Electromagnetic energy that interacts with the downhole fluid in the flow path is filtered by photonic crystal filter 343.

The spectrometer 121 includes an electromagnetic energy pump 310 such as described above. The laser gain cavity 342 is immersed in downhole fluid inside of the test cell and is in electromagnetic communication with electromagnetic energy pump 310 and photo detectors 346 and 347. In one embodiment the laser source is a rare earth doped laser gain cavity 342. In another embodiment the laser source is a number of tuned laser gain cavities 342a-342n. Each of the tuned photonic crystals receives the electromagnetic energy 301 from the laser pump and provides as output electromagnetic energy 303 that corresponds to a desired respective wavelength. A photo detector 346 senses the output band of each of the photonic crystals 342-342n. Electromagnetic energy output 303 from the photonic crystals then passes through the fluid 331 and is received by a photo detector 346, which converts the received electromagnetic energy to electrical signals that pass to the controller 358 for processing.

In another illustrative embodiment, the electromagnetic energy source 342 is a miniature laser such as a rare earth doped nanocavity laser. The high-Q nanocavity laser is miniature and can be located inside of the test cell and immersed in the fluid as shown in FIG. 4 or outside of the test cell as shown in FIG. 3. In a particular embodiment, high Q indicates a Q of about 1,000 and higher. In another particular embodiment, high Q indicates a Q of about 10,000 and higher. In another particular embodiment, high Q indicates a Q of about 100,000 and higher.

As shown in FIG. 4, one particular example of a miniature integrated circuit spectrometer 121 includes but is not limited to an electromagnetic energy source array 342 of individual electromagnetic energy sources 342a-342n positioned inside of test cell. The array 342 of this non-limiting example includes multiple electromagnetic energy sources producing infrared electromagnetic energy, for example mid-infrared electromagnetic energy, within a relatively narrow wavelength band. Alternatively, the electromagnetic energy source array 342 may produce multiple monochromatic (single wavelength) infrared electromagnetic energy from each electromagnetic energy source 342a-342n. The infrared electromagnetic energy 303 interacts with the fluid 331 in flow path 332 and at least a portion of the electromagnetic energy is reflected back to an electromagnetic energy detector 347. In the current non-limiting example the electromagnetic energy source is a laser and the electromagnetic energy detector is a photo detector. Any electromagnetic energy source and electromagnetic energy detector in accordance with the disclosure may be used in other embodiments. The photo detector 347 produces a signal responsive to the reflected electromagnetic energy, which signal is received by a processor 130 for analysis. In another embodiment the data interface 132 sends data indicative of the signals measured by photo detectors 346 and 347 to the surface controller 140 for analysis. In a particular embodiment, the photo detector 347 may be any photo detector that can detect spectra of Raman scatters corresponding to the electromagnetic energy emitted from at least one of the lasers 342a-342n. The processor 130 may further be used as a modulator for the at least one electromagnetic energy source 310 to modulate the electromagnetic energy emitted from the electromagnetic energy pump 310.

The photo detector signals are passed to the controller 358, which may include a processor 130, and memory for storing data and computer programs in a computer readable medium 134. The downhole controller 358 receives and processes the signals received from the detector 346. In one aspect, the downhole controller 358 may analyze or estimate the detected electromagnetic energy and transmit a spectrum of the Raman scattered electromagnetic energy to a surface controller 140 using data interface 132. In one aspect, the downhole controller 358 may estimate one or more properties of the downhole fluid and transmit the results to the surface controller 140 using a transmitter (not shown). In another aspect, the downhole controller 358 may process the signals received from the electromagnetic energy detector 346 to an extent and telemeter the processed data to a surface controller for producing a spectrum and for providing an in-situ estimate of a property of the fluid, including the contamination level of the mud in the formation fluid. The spectrum provided by the miniature integrated circuit spectrometer 121 may be used to estimate, for example, oil-based mud contamination and relative components in crude oils of one or more compounds in the fluid sample, such as esters or olefins.

The property of the fluid may be any desired property, including, but not limited to absorbance; refractive index; mud filtrate contamination; gas-oil ratio; oil-water ratio; gas-water ratio; an absorbance spectrum; reflectivity spectrum and a Raman spectrum. Additionally, a preprocessor associated with a controller may be located in a downhole portion of the apparatus, at the surface, or partially in the apparatus downhole and partly at the surface. In a particular illustrative embodiment, sequentially exposing the fluid to electromagnetic energy may be done by sequentially filtering the electromagnetic energy output from the plurality of lasers.

Figure 5:
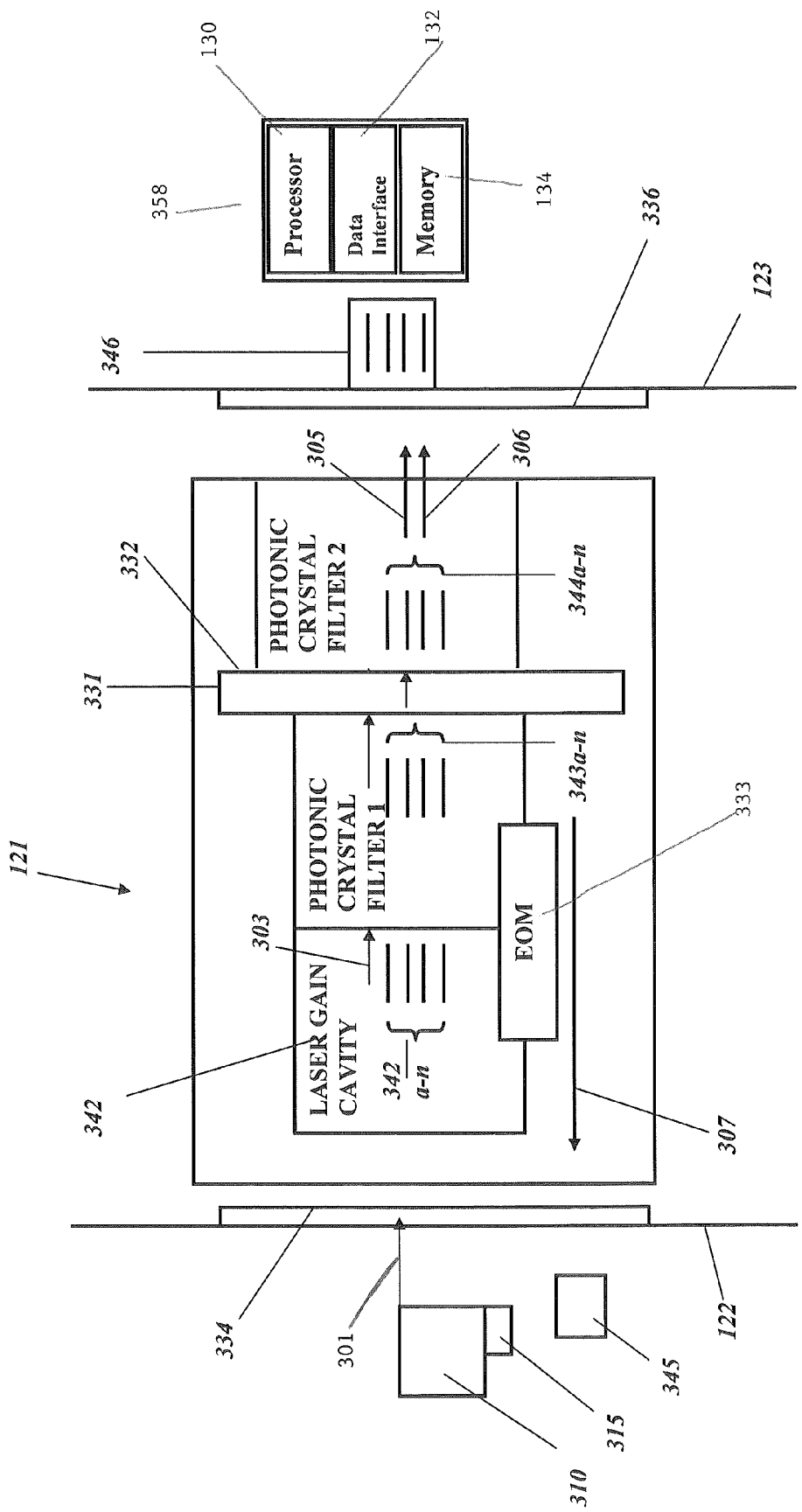
FIG. 5 is a schematic illustration of another particular illustrative embodiment according to the disclosure.

Turning now to FIG. 5, in another particular illustrative embodiment, as shown in FIG. 5, a second photonic crystal filter 344 is provided on the integrated circuit of the miniature integrated circuit spectrometer. In the embodiment of FIG. 5 the laser source which in a particular embodiment is a laser gain cavity 342 and first photonic crystal filter 343 are positioned on the integrated circuit on a first side of the fluid path and the second photonic crystal filter is positioned on a second side of the flow path 332 so that electromagnetic energy emitted from the laser gain cavity enters the first photonic crystal filter which filters the electromagnetic energy emitted from the laser source 342 before it interacts with the downhole fluid 331 in the flow path 332. Electromagnetic energy that has interacted with the downhole fluid in the fluid path is then received by the second photonic crystal filter 344. The second photonic crystal filter 344 is one or more photonic crystal filters that include a number of photonic crystal filters 344a-344n that may include but are not limited to a plurality of photonic crystal filters 344a-344n, wherein each photonic crystal is tuned by doping the photonic crystal on the integrated circuit with a particular rare earth element to provide electromagnetic energy output 305 corresponding to a distinct wavelength. Each photonic crystal laser 344a-344n in the photonic crystal filter array may be designated to correspond to a spectrometric analysis channel at a particular frequency in the miniature integrated circuit spectrometer.

In another particular embodiment, the spectrometric analysis includes but is not limited to an electromagnetic energy spectrum of interest in a range from about an ultraviolet wavelength to an infrared wavelength. In a particular illustrative embodiment the electromagnetic source may be designed to emit fluorescent stimulus electromagnetic energy at a first frequency that causes the downhole fluid in the flow path to emit a fluorescent response electromagnetic energy at a second frequency. In the embodiment of FIGS. 3 and 4, the photonic crystal filters 343 and 343a-343n are designed to receive electromagnetic energy from the downhole fluid in the flow path and substantially attenuate the fluorescent stimulus electromagnetic energy at the first frequency and substantially pass the fluorescent response electromagnetic energy at the second frequency. In the embodiment of FIG. 5 the photonic crystal filters 344 and 344a-344n are designed to receive electromagnetic energy from the downhole fluid in the flow path and substantially attenuate the fluorescent stimulus electromagnetic energy at the first frequency and substantially pass un-attenuated the fluorescent response electromagnetic energy at the second frequency.

In another particular embodiment, the electromagnetic source may also be designed to emit a selected frequency of Raman stimulus electromagnetic stimulus energy at a first frequency that causes the downhole fluid in the flow path to emit a Raman response electromagnetic energy at a second frequency including but not limited to electromagnetic energy at a Stokes and anti-Stokes frequency for the downhole fluid and the Raman stimulus frequency. The photonic crystal filters 343 and 343a-343n in the embodiment of FIG. 3 and FIG. 4 and the photonic crystal filters 344 and 344a-344n in the embodiment of FIG. 5 are designed to receive electromagnetic energy from the downhole fluid in the flow path on the miniature integrated circuit spectrometer and substantially attenuate the Raman stimulus electromagnetic energy at the first frequency and substantially pass un-attenuated the Raman response electromagnetic energy at the second frequency.

The laser gain cavity on the miniature integrated circuit spectrometer focuses electromagnetic energy at a particular frequency so that a relatively large energy density is provided in a narrow band width. The narrow bandwidth is useful in providing a concentration of electromagnetic energy with a small bandwidth of the photonic crystal filter which receives electromagnetic energy emitted from the laser source. The laser source, in the present example, a laser gain cavity focuses electromagnetic energy into a narrow bandwidth and thus provides more electromagnetic energy in the narrow bandwidth than a broad band source such as a white light. The laser gain cavity provides a higher energy density at a narrow bandwidth than a broad band source. In a particular embodiment a narrow band width is 1 megahertz. In another particular embodiment, a narrow bandwidth is 1 kilo hertz. In another particular embodiment a narrow bandwidth is 1 kilohertz. In another particular embodiment a narrow band width is 1 gigahertz. The focused electromagnetic energy provides more energy than a broad band in a narrow band to the photonic crystal filters which are tuned to a narrow band width.

In another particular illustrative embodiment, an EOM 333 is provided to tune or change the frequency of electromagnetic energy output by the laser gain cavity 342. In another particular illustrative embodiment, an EOM 333 is provided to tune or change the frequency of electromagnetic energy output by photonic crystal filter 343. In another particular illustrative embodiment, an EOM 333 is provided to tune or change the frequency of electromagnetic energy output by photonic crystal filter 344. In a particular embodiment, the laser may be any suitable type tunable laser including but not limited to the lasers, laser gain cavities, photonic crystals and other laser types described herein. In a particular embodiment, an EOM applies thermal energy to the laser to change the frequency of the electromagnetic energy emitted by the laser. In another embodiment the EOM applies mechanical stress from a mechanical or piezoelectric device to change the frequency of the electromagnetic energy emitted by the laser gain cavity and/or photonic crystal filter. In a particular embodiment the EOM is integrated onto silicon wafer with the laser for control of each of the laser's and/or filters output electromagnetic energy wavelength. In another illustrative embodiment, the EOM applies thermal energy or stress to more than one laser gain cavity, laser or photonic crystal at a time to tune the lasers and/or photonic crystals in groups of 2 or more. In another illustrative embodiment, the EOM tunes each laser or filter in a group of lasers or filters one at a time or individually. The integrated circuit can be manufactured on any suitable material, including but not limited to silicon, silicon oxide, indium phosphide and gallium arsenide.

In a preferred embodiment, the electromagnetic energy from the laser gain cavity interacts with the downhole fluid in the flow path and subsequently filtered by photonic crystal filter 343. Electromagnetic energy from each photonic crystal filter may be detected by a common or separate photo detector 346. For example, a single photo detector 346 or an array of photo detectors 346a-346n may be used to detect electromagnetic energy from a corresponding laser gain cavity 342a-342n. An interface circuit in processor 132 receives a measurement of electromagnetic energy from the photo detectors 346a-346n, which can include but is not limited to a fluorescence electromagnetic energy measuring device and a Raman scattering Stokes and anti Stokes electromagnetic energy measuring device and converts the received measurement of electromagnetic energy into digital signals and provides the digital signals to downhole controller 358. The downhole controller 358 may include a processor 130, which may be a microprocessor, a set of computer programs stored in a memory including but not limited to non-transitory tangible computer readable medium 134 that is in data communication with the processor 130. In a particular embodiment, the downhole processor processes the data received from the photodetector 346 to estimate a property of the downhole fluid. The downhole processor also controls the EOM to determine the frequency of electromagnetic energy emitted by each electromagnetic source, laser gain cavity and photonic crystal filter. The controller may be disposed in the downhole tool or at the surface. Alternatively, the data may be processed to a certain extent downhole by a first controller 358 deployed in the tool and the remaining processing may be accomplished at the surface by another suitable controller, such as surface controller 140 (FIG. 1). Data communication, that sending and receiving data between the downhole controller and the surface controller may be managed via any suitable telemetry link, such as a data link from processor data interface 132 in controller 358 to surface controller 140. The data link may be any suitable data transmission medium in accordance with the disclosure, including but not limited to a wireline, wired pipe, mud pulse telemetry, acoustic telemetry, and electromagnetic telemetry, etc.

Electromagnetic energy that has interacted with the fluid passes through windows 336 and 334. Electromagnetic energy that passes through window 336 is received by photo detector 346 which may be an array of photo detectors 346a-346n.

A UV laser, broad band white light source or another suitable electromagnetic energy source 310 is provided to introduce electromagnetic energy to laser gain cavity 342 which emits electromagnetic energy 303 to downhole fluid 331 in the flow path. In a particular embodiment, electromagnetic energy is pumped by the laser pump within a relatively narrow UV wavelength band tuned to produce monochromatic (substantially single wavelength) UV electromagnetic energy. The electromagnetic energies 304, 305, 306 and 307 that have interacted with the fluid 331 are detected by the photo detector modules 346 and 347. Photo detectors 346 and 347 may each be a singular or plurality of photo detectors in an array of photo detectors as discussed above regarding photo detector 346. In a particular embodiment, the photodetector array includes but is not limited to an array of photonic crystals tuned to pass a selected spectrum of electromagnetic energy and provide such spectrum to the processor 130 for analysis. Alternatively, reflected electromagnetic energy 307 reflected from the downhole fluid may be detected for estimating a property of the downhole fluid. In another embodiment Raman response electromagnetic energy including but not limited to Stokes and anti-Stokes electromagnetic energy 306 is measured by electromagnetic sensor 346, which can be a photo detector for estimating in-situ a property of the fluid 331. Processor 130 executes computer program instructions stored in memory embedded in computer readable medium 134 on downhole controller 358.

Raman spectroscopy is a spectroscopic technique based on inelastic scattering of monochromatic light, usually from a laser source. Inelastic scattering means that the frequency of photons in monochromatic light changes upon interaction with a sample. Photons of the laser light are absorbed by the sample and then reemitted. Frequency of the reemitted photons is shifted up or down in comparison with original monochromatic frequency, which is called the Raman effect. This shift provides information about vibrational, rotational and other low frequency transitions in molecules. Raman spectroscopy can be used to study solid, liquid and gaseous samples. The Raman effect is based on molecular deformations in electric field E determined by molecular polarizability $\alpha$. The laser beam can be considered as an oscillating electromagnetic wave with electrical vector E. Upon interaction with the sample it induces electric dipole moment $P=\alpha E$ which deforms molecules. Because of periodical deformation, molecules start vibrating with characteristic frequency $\upsilon m$.

Amplitude of vibration is called a nuclear displacement. In other words, monochromatic laser light with frequency $\upsilon 0$ excites molecules and transforms them into oscillating dipoles. Such oscillating dipoles emit light of three different frequencies. When a molecule with no Raman-active modes absorbs a photon with the frequency $\upsilon 0$. The excited molecule returns back to the same basic vibrational state and emits light with the same frequency $\upsilon 0$ as an excitation source. This type of interaction is called an elastic Rayleigh scattering. A photon with frequency $\upsilon 0$ is absorbed by Raman-active molecule which at the time of interaction is in the basic vibrational state. Part of the photon's energy is transferred to the Raman-active mode with frequency $\upsilon m$ and the resulting frequency of scattered light is reduced to $\upsilon 0 \upsilon m$.

This Raman frequency is called Stokes frequency, or just "Stokes". A photon with frequency υ0 is absorbed by a Raman-active molecule, which, at the time of interaction, is already in the excited vibrational state. Excessive energy of excited Raman active mode is released, molecule returns to the basic vibrational state and the resulting frequency of scattered light goes up to υ0+υm. This Raman frequency is called Anti Stokes frequency, or just "Anti-Stokes".

Fluorescence spectroscopy, also referred to as fluorometry or spectrofluorometry, is a type of electromagnetic spectroscopy which analyzes fluorescence from a sample. It involves using a beam of light, usually ultraviolet light, that excites the electrons in molecules of certain compounds and causes them to emit light of a lower energy, typically, but not necessarily, visible light. A complementary technique is absorption spectroscopy.

Devices that measure fluorescence are provided as a photo detector called fluorometers or fluorimeters. Molecules have various states referred to as energy levels. Fluorescence spectroscopy is primarily concerned with electronic and vibrational states. Generally, the species being examined has a ground electronic state (a low energy state) of interest, and an excited electronic state of higher energy. Within each of these electronic states are various vibrational states. In fluorescence spectroscopy, the species is first excited, by absorbing a photon, from its ground electronic state to one of the various vibrational states in the excited electronic state. Collisions with other molecules cause the excited molecule to lose vibrational energy until it reaches the lowest vibrational state of the excited electronic state. The molecule then drops down to one of the various vibrational levels of the ground electronic state again, emitting a photon in the process. As molecules may drop down into any of several vibrational levels in the ground state, the emitted photons will have different energies, and thus frequencies. Therefore, by analyzing the different frequencies of light emitted in fluorescent spectroscopy, along with their relative intensities, the structure of the different vibrational levels can be determined. In a particular embodiment, different wavelengths of fluorescent light emitted by a sample are measured using a monochromator, holding the excitation light at a constant wavelength. This is called an emission spectrum. An excitation spectrum is the opposite, whereby the emission light is held at a constant wavelength, and the excitation light is scanned through many different wavelengths (via a monochromator). An Emission Map is measured by recording a number of different emission spectra created from different excitation wavelengths, and combining them all together. This is a three dimensional data set, intensity of emission as a function of excitation and emission wavelengths, and is typically depicted as a contour map. A property of the downhole fluid such as the presence of a particular compound or gas oil ratio can be determined using fluorescent spectroscopy.

The electromagnetic energy emitted from the electromagnetic energy source 310 or laser source array 342 may be modulated by a processor 130 within the same downhole controller 358 that receives the photodetector output or by a separate modulator in a second controller 315 including but not limited to a processor, computer readable medium and data interface (not shown for simplicity). In a particular embodiment, controller 358 is in data communication with the photodetector 334 and a second controller 315 is in data communication with the EOM 333 for modulating electromagnetic energy emitted by the electromagnetic energy source 310 or the laser source array 342 respectively. These controllers may be implemented as a single controller downhole without departing from the scope of the disclosure. In other embodiments, the controller or controllers may be located at the surface of the well borehole. For purposes of this description, when two things are in "data communication" they can send and receive data from each other and when two things are in "electromagnetic communication" one sends electromagnetic energy that is received by the other.

In wireline embodiments, communication may be accomplished via the wireline cable. In while-drilling embodiments, communication may be accomplished via wired pipe, acoustic pipe communication, or by mud-pulse telemetry. In wireline embodiments disclosed herein, the electromagnetic energy source 310 or array 342 may be located at a well borehole surface location and the electromagnetic energy path may include one or more optical fibers extending from the surface location to the downhole tool using the wireline cable as a support.

The electromagnetic energy source 310 or laser gain cavity 342 may include one or more electromagnetic energy emitting semiconductors used as the individual electromagnetic energy sources 342a-342n. For example, the one or more electromagnetic energy sources 342 and/or 342a-342n may include one or more rare earth doped laser fibers, rare earth doped laser wafers, rare earth doped silicon on insulator lasers, which may include one or more ridge waveguide quantum cascade lasers, one or more buried hetero structure waveguide quantum cascade lasers (QCL), one or more Fabry Perot quantum cascade lasers, one or more distributed feedback ("DFB") quantum cascade lasers, a SLED, one or more distributed Bragg reflector ("DBR") quantum cascade lasers, or any combination thereof. As used herein, "QCL," refers generally to quantum cascade lasers, types of which may include but are not limited to ridge waveguide quantum cascade lasers, buried hetero structure waveguide quantum cascade lasers, Fabry Perot quantum cascade lasers, DFB quantum cascade lasers and DBR quantum cascade lasers. Quantum cascade lasers exhibit relatively narrow line widths and are wavelength tunable. The individual electromagnetic energy sources may be operated continuously or in a pulsed mode to emit an electromagnetic energy of a selected wavelength or wavelengths toward the downhole fluid in the test cell. In several non-limiting embodiments, the individual electromagnetic energy sources can emit electromagnetic energy in the infrared region. The wavelength of lasers may be changed such that the derivative of the spectra may be measured which can remove the requirement for background calibration.

Multiple wavelengths of electromagnetic energy emitted by lasers arranged in an array may be detected using a single photodetector. Photo detectors typically experience drift with respect to another as temperature increases, meaning that the response characteristics of each photodetector is unique when subjected to temperature fluctuations. Using a single photodetector reduces the need to account for differences in how one photodetector drifts with respect to other photo detectors.

Each laser gain cavity 342a-342n can be configured or selected to emit an electromagnetic energy having a wavelength corresponding to a different optical channel of the miniature integrated circuit spectrometer 121. In one embodiment, modulating the electromagnetic energy sources includes turning each electromagnetic energy source on individually and sequentially using the controller 358 and EOM 333 so that each electromagnetic energy source in the array 342 emits a specific wavelength of electromagnetic energy through the fluid 331 in test cell at a different time. In another embodiment, each source in the array 342 emits at the same time. In a particular embodiment, each laser gain cavity in array 342 can be tuned individually or in a group of two or more by EOM 333.

Maintaining the at least one electromagnetic energy source on the miniature integrated circuit spectrometer at a constant temperature helps to provide wavelength stability. In one embodiment, the electromagnetic energy source array is maintained at a substantially constant temperature by EOM 333. In another embodiment the wavelength of each electromagnetic energy source is modulated by rapidly changing its temperature over a small temperature range. This rapid temperature change can be accomplished by rapidly changing the current through the electromagnetic energy source or by changing electrical current supplied to auxiliary resistive heaters in thermal contact with each electromagnetic energy source. In another embodiment the wavelength is modulated by using an external cavity. Alternatively, each electromagnetic energy source's wavelength could be modulated using EOM 333 to modulate the electromagnetic energy source's temperature, which is done most easily by modulating the current through it or by providing a heater or stressor (piezoelectric or mechanical) adjacent the electromagnetic energy source to modulate the frequency of electromagnetic energy out put. The frequency modulation enables performance of derivative spectroscopy with helps to find small peaks on an amplitude spectrum curve.

In another embodiment, the wavelength of each of the laser gain cavities 342a-342n may be modulated to each emit a different frequency, which saves time through the multiplexing advantage associated with measuring all wavelengths simultaneously with a single photodetector. Then, the output of the photodetector can be filtered (digitally or in hardware) to recover that portion of the photodetector response that is the result of any particular laser.

In another embodiment, apparatus for estimating a property of a downhole fluid is disclosed, the apparatus including but not limited to a carrier that is conveyable in a borehole; a test cell carried by the carrier for capturing the downhole fluid; an integrated circuit positioned inside of the test cell; an electromagnetic energy source that emits an electromagnetic energy beam having a first bandwidth; a first filter formed on the integrated circuit in electromagnetic energy communication with the first electromagnetic energy beam, that filters the electromagnetic energy beam and passes through a portion of the electromagnetic energy beam having a second bandwidth that is narrower than the first bandwidth; a flow path formed in the integrated circuit wherein the flow path contains the downhole fluid in the test cell and is in electromagnetic energy communication with a portion of the electromagnetic energy beam; and an electromagnetic energy detector in electromagnetic energy communication with a portion of the electromagnetic energy beam that has interacted with the downhole fluid for estimating the property of the downhole fluid. In another embodiment of the apparatus the flow path is positioned between the electromagnetic energy source and the first filter.

In another embodiment of the apparatus the electromagnetic energy source emits electromagnetic energy at a stimulus frequency into the downhole fluid in the flow path and wherein the first filter filters out electromagnetic energy received from the downhole fluid in the flow path at the stimulus frequency and passes electromagnetic energy centered around a response frequency from the downhole fluid. In another embodiment of the apparatus the stimulus frequency is centered about a Raman excitation frequency for the downhole fluid and the response frequency is centered around a Stokes frequency. In another embodiment of the apparatus the stimulus frequency is centered about a fluorescent excitation frequency for the downhole fluid and the response frequency is centered about a fluorescent frequency for the downhole fluid. In another embodiment of the apparatus the apparatus further includes but is not limited to a second filter formed on the integrated circuit and positioned in electromagnetic energy communication with the portion of the electromagnetic energy beam passed by the first filter, wherein the flow path is positioned on the integrated circuit between the first filter and the second filter.

In another embodiment of the apparatus the electromagnetic energy detector is a photo detector and the electromagnetic energy source is a laser gain cavity having a quality factor, Q of at least about 100,000. In another embodiment of the apparatus the laser source is a rare earth doped laser gain cavity formed on the integrated circuit and the first filter and second filters are photonic crystals formed on the integrated circuit. In another embodiment of the apparatus the electromagnetic energy source further includes but is not limited to an electro optic modulator integrated into the integrated circuit for adjusting a frequency of laser light emitted from the laser gain cavity to a wavelength of interest for detecting the property of the downhole fluid. In another embodiment of the apparatus the electro optic modulator is a thermal controller.

In another embodiment of the apparatus the electro optic modulator device is an integrated circuit is at least one of an integrated stress tuner and a thermal tuner and wherein the laser further comprises a plurality of rare earth doped laser gain cavities integrated on a wafer with the electro optic modulator, wherein each of the plurality of rare earth doped lasers' frequency of electromagnetic energy output is tunable using the electro optic modulator. In another embodiment of the apparatus the integrated circuit has a volume of about 1 cubic centimeter electromagnetic source further comprises a nanocavity in a two-dimensional photonic crystal slab wherein a Q for the rare earth doped laser is higher than about 1000. In another embodiment of the apparatus the apparatus further includes but is not limited to an electromagnetic energy pump located outside of the test cell; a window formed in a side of the test cell for ingress and egress of electromagnetic energy to and from the test cell, wherein electromagnetic energy detector and the electromagnetic energy pump are located outside of the test cell and the electromagnetic energy source is located inside of the test cell, wherein the electromagnetic energy pump further comprises gratings, each of which reflect electromagnetic energy at a frequency of interest from electromagnetic energy that has interacted with the fluid, to detect a compound of interest in the fluid.

In another embodiment of the apparatus the electromagnetic energy that has interacted with the fluid is at least one of electromagnetic energy that has passed through the downhole fluid, electromagnetic energy that fluoresces from the downhole fluid and electromagnetic energy that has reflected off of the downhole fluid, wherein the filter further comprises a plurality of gratings, each of which reflect electromagnetic energy at a frequency of interest from electromagnetic energy that has interacted with the fluid, to detect a compound of interest in the fluid, the apparatus further including but not limited to a processor configured to analyze the electromagnetic energy that has interacted with the downhole fluid for transmittance, fluorescence, absorbance and reflectance.

In another embodiment a method for estimating a property of a downhole fluid is disclosed, the method including but not limited to capturing a downhole fluid in a test cell; generating an electromagnetic energy beam centered around an excitation frequency; introducing the electromagnetic energy beam into the downhole fluid in a flow path on an integrated circuit;

filtering on the integrated circuit, the electromagnetic energy emitted from the downhole fluid in the flow path while passing electromagnetic energy at a response frequency from the downhole fluid substantially un-attenuated and substantially attenuating electromagnetic energy at the excitation frequency; and measuring the electromagnetic energy at the response frequency received from the downhole fluid for estimating the property of the downhole fluid. In another embodiment of the method, the electromagnetic energy beam is generated in a laser gain cavity on the integrated circuit, wherein the laser gain cavity is a rare earth doped fiber laser.

In another embodiment of the method, the method further includes but is not limited to adjusting a frequency of the rare earth doped laser gain cavity to a wavelength of interest using an electro optic modulator for detecting the presence of a chemical of interest in the fluid for estimating the property of the downhole fluid. In another embodiment of the method, the electro optic modulator device is at least one of a piezoelectric stress tuner, a mechanical stress tuner and a thermal tuner. In another embodiment of the method, the rare-earth doped laser gain cavity further comprises a nanocavity in a two-dimensional photonic crystal slab wherein a Q for the rare-earth doped gain cavity is higher than about 1000 and the integrated circuit has a volume of less that 1 cubic centimeter. In another embodiment of the method, the electromagnetic energy that has interacted with the fluid is at least one of electromagnetic energy that has passed through the fluid, electromagnetic energy that has reflected off of the downhole fluid, electromagnetic energy that responds to the interaction by fluorescence in the downhole fluid and electromagnetic energy that responds to the interaction by emitting electromagnetic energy centered about a Raman Stokes frequency, and the method further including but not limited to analyzing the electromagnetic energy that has interacted with the fluid for at least one of transmittance, fluorescence, absorbance, Raman scattering and reflectance; and estimating the property of the downhole fluid based on the analyzing.

In another embodiment an apparatus for estimating a property of a downhole fluid, the apparatus including but not limited to an electromagnetic energy source that emits an electromagnetic energy beam having a first bandwidth; a first filter formed on the integrated circuit in electromagnetic energy communication with the first electromagnetic energy beam, that filters the electromagnetic energy beam to provide a second electromagnetic energy beam having a second bandwidth that is narrower than the first bandwidth and that interacts with the downhole fluid; and an electromagnetic energy detector in electromagnetic energy communication with at least a portion of the second electromagnetic energy beam that has interacted with the downhole fluid, the electromagnetic energy providing a signal that is processed by a processor for estimating the property of the downhole fluid.

Referring now to the several non-limiting illustrative embodiments described above and shown in the figures, one skilled in the art with the benefit of the present disclosure will better understand several non-limiting operational examples. An optical absorption spectrum can be generated using single-pass and/or multiple-pass absorption spectroscopy to indicate the presence of one or more specified molecules in a fluid sample. Oil-based mud filtrate often has a distinct spectral signature due to the presence of olefins and esters, which do not naturally occur in crude oils. For example, olefins produce peaks in the mid-infrared region from about 800 $cm^{-1}$ to about 1000 $cm^{-1}$ and esters produce peaks from about 1,600 $cm^{-1}$ to about 1,800 $cm^{-1}$. In operation, the downhole spectrometer can be used to estimate the percentage of oil based mud filtrate contamination of crude oil samples as they are being collected downhole. One can continue withdrawing and discarding oil removed from the downhole formation until the contamination falls below a desired level and then diverts a clean fluid sample being withdrawn into a sample collection tank.

In some embodiments, a tool such as the miniature integrated circuit spectrometer described above may be used for permanent well monitoring. In these embodiments, the spectrometer or at least a portion of the spectrometer may be installed within a producing well to monitor production of downhole fluids. In some cases, producing wells may produce harmful compounds and/or gasses that may cause damage to equipment or present hazards at a well site. In one example, the method includes monitoring a producing well to estimate production downhole fluid properties. The fluid properties may include the presence of harmful compounds such as hydrogen sulfide, carbonyl sulfide, cyanide, hydrogen cyanide, sulfur dioxide, and brine.

In at least one embodiment, one or more miniature integrated circuit spectrometers or at least a portion of the miniature integrated circuit spectrometers, as described and discussed above, may be used to periodically or continuously monitor production of downhole fluids. For example, one or more readings can be taken with at least one spectrometer every 30 seconds, minute, two minutes, 5 minutes, one-half hour, hour, two hours, or any periodic interval desired. In another example, at least one miniature integrated circuit spectrometer can continually acquire data which can be processed in real time or stored and, if desired, later analyzed to provide a continuous monitoring of the production of downhole fluids as it is acquired.

Having described above the several aspects of the disclosure, one skilled in the art will appreciate several particular embodiments useful in determining a property of an earth subsurface structure using a downhole spectrometer. The present disclosure is to be taken as illustrative rather than as limiting the scope or nature of the claims below. Numerous modifications and variations will become apparent to those skilled in the art after studying the disclosure, including use of equivalent functional and/or structural substitutes for elements described herein, use of equivalent functional couplings for couplings described herein, and/or use of equivalent functional actions for actions described herein. Such insubstantial variations are to be considered within the scope of the claims below.

Given the above disclosure of general concepts and specific embodiments, the scope of protection is defined by the claims appended hereto. The issued claims are not to be taken as limiting Applicant's right to claim disclosed, but not yet literally claimed subject matter by way of one or more further applications including those filed pursuant to the laws of the United States and/or international treaty.

What is claimed is:

1. An apparatus for estimating a property of a downhole fluid, the apparatus comprising:
  a carrier that is conveyable in a borehole;
  a test cell carried by the carrier for capturing the downhole fluid;
  an integrated circuit positioned inside of the test cell;
  an electromagnetic energy source that emits an electromagnetic energy beam having a first bandwidth;
  a first filter formed on the integrated circuit in electromagnetic energy communication with the first electromagnetic energy beam, that filters the electromagnetic energy beam and passes through a portion of the electromagnetic energy beam having a second bandwidth that is narrower than the first bandwidth;

a flow path formed in the integrated circuit wherein the flow path contains the downhole fluid in the test cell and is in electromagnetic energy communication with the portion of the electromagnetic energy beam having the second bandwidth; and an electromagnetic energy detector in electromagnetic energy communication with a portion of the electromagnetic energy beam that has interacted with the downhole fluid for estimating the property of the downhole fluid.

2. The apparatus of claim 1, wherein the first filter is positioned between the electromagnetic energy source and the flow path.

3. The apparatus of claim 2, wherein the electromagnetic energy source emits electromagnetic energy at a stimulus frequency and the portion of the electromagnetic energy beam that has interacted with the downhole fluid in the flow path includes a response frequency.

4. The apparatus of claim 3, wherein the stimulus frequency is centered about a Raman excitation frequency for the downhole fluid and the response frequency is centered around a Stokes frequency.

5. The apparatus of claim 3, wherein the stimulus frequency is centered about a fluorescent excitation frequency for the downhole fluid and the response frequency is centered about a fluorescent frequency for the downhole fluid.

6. The apparatus of claim 1, the apparatus further comprising:
a second filter formed on the integrated circuit and positioned in electromagnetic energy communication with the portion of the electromagnetic energy beam passed by the first filter, wherein the flow path is positioned on the integrated circuit between the first filter and the second filter.

7. The apparatus of claim 6, wherein the electromagnetic energy source is a rare earth doped laser gain cavity formed on the integrated circuit and the first filter and second filters are photonic crystals formed on the integrated circuit.

8. The apparatus of claim 6, wherein the electromagnetic energy that has interacted with the fluid is at least one of electromagnetic energy that has passed through the downhole fluid, electromagnetic energy that fluoresces from the downhole fluid or electromagnetic energy that has reflected off of the downhole fluid, and the second filter further comprises a plurality of gratings, each of which reflect electromagnetic energy at a frequency of interest from electromagnetic energy that has interacted with the fluid, to detect a compound of interest in the fluid, the apparatus further comprising:
a processor configured to analyze the electromagnetic energy that has interacted with the downhole fluid for transmittance, fluorescence, absorbance and reflectance.

9. The apparatus of claim 1, wherein the electromagnetic energy detector is a photo detector and the electromagnetic energy source is a laser gain cavity having a quality factor, Q of at least about 100,000.

10. The apparatus of claim 1, wherein the electromagnetic energy source further comprises:
an electro optic modulator integrated into the integrated circuit for adjusting a frequency of laser light emitted from the laser gain cavity to a wavelength of interest for detecting the property of the downhole fluid.

11. The apparatus of claim 10, wherein the electro optic modulator is a thermal controller.

12. The apparatus of claim 10, wherein the electro optic modulator is at least one of an integrated stress tuner and a thermal tuner and wherein the laser further comprises a plurality of rare earth doped laser gain cavities integrated on a wafer with the electro optic modulator, wherein each of the plurality of rare earth doped lasers' frequency of electromagnetic energy output is tunable using the electro optic modulator.

13. The apparatus of claim 1, wherein the integrated circuit has a volume of about 1 cubic centimeter electromagnetic source further comprises a nanocavity in a two-dimensional photonic crystal slab wherein a Q for the rare earth doped laser is higher than about 1000.

14. The apparatus of claim 1, the apparatus further comprising:
an electromagnetic energy pump located outside of the test cell;
a window formed in a side of the test cell for ingress and egress of electromagnetic energy to and from the test cell, wherein the electromagnetic energy detector and the electromagnetic energy pump are located outside of the test cell and the electromagnetic energy source is located inside of the test cell, wherein the electromagnetic energy pump further comprises gratings, each of which reflect electromagnetic energy at a frequency of interest from electromagnetic energy that has interacted with the fluid, to detect a compound of interest in the fluid.

15. A method for estimating a property of a downhole fluid, the method comprising:
capturing a downhole fluid in a test cell;
generating an electromagnetic energy beam centered around an excitation frequency in a laser gain cavity on an integrated circuit, wherein the laser gain cavity is a rare earth doped fiber laser;
introducing the electromagnetic energy beam into the downhole fluid in a flow path on the integrated circuit;
filtering, on the integrated circuit, the electromagnetic energy emitted from the downhole fluid in the flow path while passing electromagnetic energy at a response frequency from the downhole fluid substantially un-attenuated and substantially attenuating electromagnetic energy at the excitation frequency; and
measuring the electromagnetic energy at the response frequency received from the downhole fluid for estimating the property of the downhole fluid.

16. The method of claim 15, the method further comprising:
adjusting a frequency of the rare earth doped laser gain cavity to a wavelength of interest using an electro optic modulator for detecting the presence of a chemical of interest in the fluid for estimating the property of the downhole fluid.

17. The method of claim 16, wherein the electro optic modulator device is at least one of a piezoelectric stress tuner, a mechanical stress tuner or a thermal tuner.

18. The method of claim 17, wherein the rare-earth doped laser gain cavity further comprises a nanocavity in a two-dimensional photonic crystal slab wherein a Q for the rare-earth doped gain cavity is higher than about 1000 and the integrated circuit has a volume of less than 1 cubic centimeter.

19. The method of claim 15, wherein the electromagnetic energy that has interacted with the fluid is at least one of electromagnetic energy that has passed through the fluid, electromagnetic energy that has reflected off of the downhole fluid, electromagnetic energy that responds to the interaction by fluorescence in the downhole fluid or electromagnetic energy that responds to the interaction by emitting electromagnetic energy centered about a Raman Stokes frequency, and the method further comprises analyzing the electromagnetic energy that has interacted with the fluid for at least one of transmittance, fluorescence, absorbance, Raman scattering and reflectance; or estimating the property of the downhole fluid based on the analyzing.

20. An apparatus for estimating a property of a downhole fluid, the apparatus comprising:
- an electromagnetic energy source that emits an electromagnetic energy beam having a first bandwidth;
- a first filter formed on the integrated circuit in electromagnetic energy communication with the first electromagnetic energy beam, that filters the electromagnetic energy beam to provide a second electromagnetic energy beam having a second bandwidth that is narrower than the first bandwidth and that interacts with the downhole fluid; and
- an electromagnetic energy detector in electromagnetic energy communication with at least a portion of the second electromagnetic energy beam that has interacted with the downhole fluid, the electromagnetic energy providing a signal that is processed by a processor for estimating the property of the downhole fluid.

* * * * *